Figure 1:
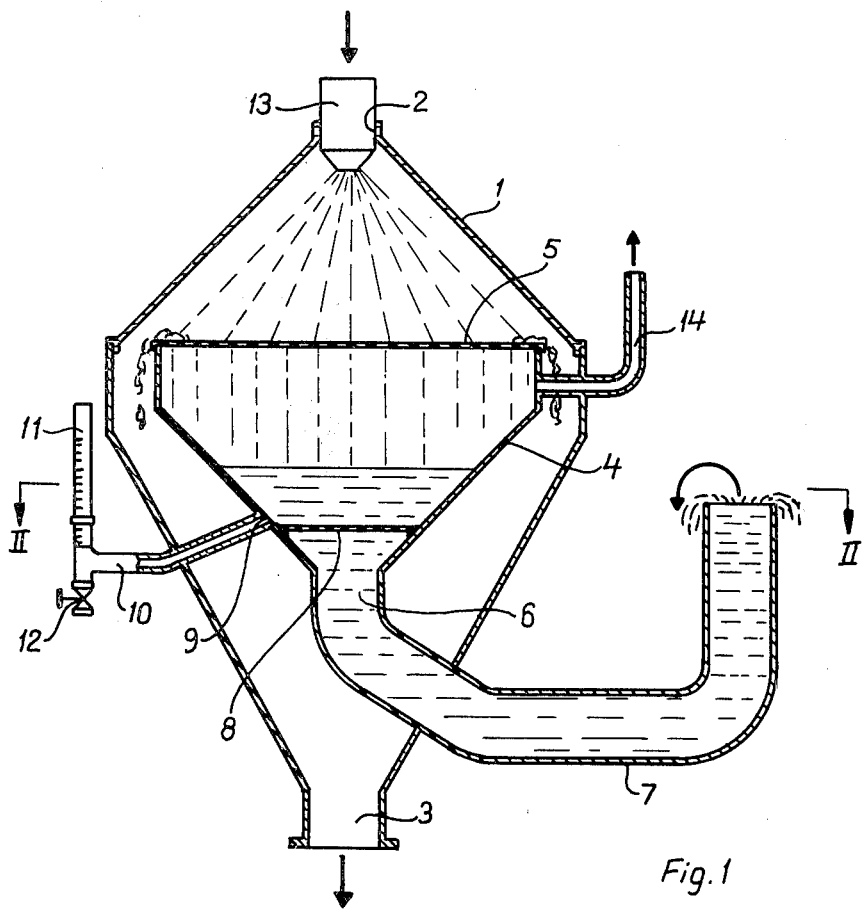

United States Patent

Rundqvist et al.

[11] 3,935,109
[45] Jan. 27, 1976

[54] STRAINING APPARATUS

[75] Inventors: Lars-Goran Rundqvist, Tumba; Karl Folke Olof Jakobson, Taby, both of Sweden

[73] Assignee: AB Celleco, Tumba, Sweden

[22] Filed: Oct. 18, 1973

[21] Appl. No.: 407,589

[30] Foreign Application Priority Data
Oct. 25, 1972 Switzerland............... 13740/72

[52] U.S. Cl............... 210/406; 210/416; 209/250; 209/273; 209/355
[51] Int. Cl.²............................................ B01D 35/00
[58] Field of Search .......... 210/256, 258, 299, 300, 210/307, 315, 316, 406, 416, 474, 477, 482, 314, 335, 339, 86, 93; 209/250, 358, 359, 389, 390, 273, 17, 268, 355; 162/242, 251

[56] References Cited
UNITED STATES PATENTS

| | | |
|---|---|---|
| 2,860,784 | 11/1958 | Breithaupt............................ 210/90 |
| 2,874,840 | 2/1959 | Simpson............................ 209/250 |
| 2,901,763 | 9/1959 | Jalkanen............................ 210/415 |
| 2,988,223 | 6/1961 | Janson............................ 209/250 |
| 3,003,642 | 10/1961 | Ulrich............................ 210/335 |
| 3,004,669 | 10/1961 | Ulrich............................ 210/335 |
| 3,024,911 | 3/1962 | Samson............................ 209/268 |
| 3,474,911 | 10/1969 | Olsen............................ 210/346 |
| 3,506,121 | 4/1970 | Holm............................ 209/355 |
| 3,789,978 | 2/1974 | Janson............................ 209/250 |

Primary Examiner—Charles N. Hart
Assistant Examiner—F. F. Calvetti
Attorney, Agent, or Firm—Cyrus S. Hapgood

[57] ABSTRACT

A fibre-containing liquid is sprayed on the inlet side of a first strainer, there being a flow path for medium passing therethrough and leading from the outlet side of the strainer. A second strainer spaced from the first strainer covers said flow path and has mesh openings larger than those of the first strainer but small enough so that fibres passing through the first strainer, due to rupture thereof, will rapidly obstruct the second strainer.

5 Claims, 2 Drawing Figures

STRAINING APPARATUS

The present invention relates to a straining apparatus for separating fibres and the like from a liquid that is sprayed on the strainer.

It has long been desired that apparatus of this kind should be suitable for freeing so-called backwater, coming from a paper-making machine, from fibres present therein, so that the water can be re-used in the paper-making machine as so-called spray-water. Spray-water is sprayed on the paper-making machine wire through nozzles having very narrow channels.

At present, filters of different kinds are used for separating fibres from backwater. These filters become clogged by separated fibres, however, and must be cleansed at certain time intervals. Filters of this kind are also expensive. Straining apparatus of the first-described kind, in which a liquid is sprayed on a strainer, are self-cleansing and may, therefore, be in operation continuously during long periods of time. This is one of the reasons why they are also cheaper in most cases than conventional filter apparatus.

The main reason why straining apparatus of this kind has not been used for separating fibres from backwater coming from a paper-making machine is that rupture of the strainer, which sometimes occurs, would lead to very severe consequences. The strainer usually consists of a fine-mesh net of thin threads which can easily burst if they are hit by some strange object present in the liquid that is sprayed on the strainer. In case of rupture of the strainer, the fibres present in the backwater will immediately block the channels in the nozzles in the paper-making machine. Sooner or later this will lead to rupture of the running wire of the paper-making machine, causing heavy expenses, and will also necessitate far-reaching and time-consuming work for cleaning the nozzles.

An object of the present invention is to solve this problem, so that straining apparatus of the first-mentioned kind can be used for the above-mentioned and similar purposes.

This object is achieved by providing the straining apparatus with means comprising a further strainer arranged on the outlet side of the first strainer and spaced therefrom, which further strainer covers the flow path for medium having passed through the first strainer, the mesh openings of the further strainer being larger than the mesh openings of the first strainer but not larger than required so that fibres having passed through the first strainer (due to rupture of it) will rapidly obstruct the further strainer.

During test runs with an apparatus of this kind, the further strainer has been immediately obstructed also upon minor rupture of the first strainer, and no long fibres have passed through the further strainer in spite of the fact that it has had larger mesh openings than the first strainer. A particularly rapid obstruction of the further strainer has been obtained when the apparatus also comprised means for maintaining, during the operation of the straining apparatus, a liquid column covering the inlet side of the further strainer. Another factor that is important for a rapid obstruction of the further strainer is that the latter is smaller than the first strainer.

For maintaining a liquid column covering the inlet side of the further strainer, no other means are required than walls confining a liquid column. If desired, the throughflow area and/or the mesh openings of the further strainer may be so small that the strainer itself constitutes a throttling in the flow path of the liquid for forming and maintaining the liquid column. It is not preferable, however, to have a substantial pressure drop across the further strainer during normal operation of the straining apparatus, and therefore other measurements are preferably taken for maintaining a water column having a certain minimum height above the further strainer. Due to the presence of the liquid column, there is no risk of making the mesh openings of the further strainer much larger than the mesh openings of the first strainer. This is a guarantee for an undisturbed normal operation of the straining apparatus owing to the fact that the further strainer, which unlike the first strainer is not subjected to syringing with liquid, will easily let through particles which have been able to pass through the first strainer only because of the said syringing of the liquid.

In a preferred embodiment of the invention, there is also an arrangement for indicating an obstruction of the further strainer and an arrangement for rapid cleansing of the further strainer after such an obstruction. The advantages of such arrangements will be seen from the following description of the invention with reference to the accompanying drawing.

Figure 2:
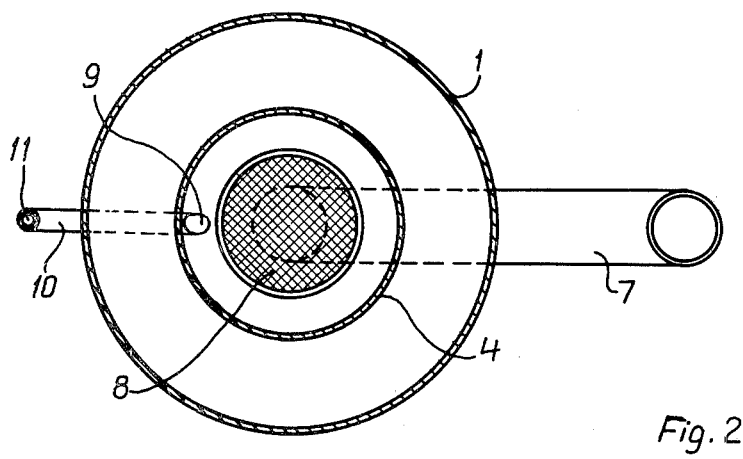

In the accompanying drawing,

FIG. 1 is a longitudinal sectional view of a straining apparatus according to the invention, and FIG. 2 is a cross-sectional view along the line II–II in FIG. 1.

In a casing 1 having an inlet 2 at the top and an outlet 3 at the bottom, there is arranged a funnel-shaped vessel 4. The vessel 4 opens upwardly and is covered by a strainer 5 in the form of a net, the mesh openings of which are carefully determined, for instance 0.16 mm. The vessel 4 at its bottom has an outlet 6 to which is connected a conduit 7 extending through the wall of the casing 1 and opening outside this wall at a level above the outlet 6. Above the outlet 6 there is arranged a further strainer 8, the mesh openings of which are larger than the mesh openings of the first strainer 5, for instance 2.0 mm.

Immediately above the further strainer 8, the vessel 4 has a further outlet 9. To this outlet 9 there is connected a conduit 10 extending out through the wall of the casing 1 and opening into a vertical tube 11. The tube 11, being open at the top, has a lower portion situated at a level below the further strainer 8. The lower end of the tube 11 is closed by means of a shut-off valve 12.

Numeral 13 designates a nozzle which is arranged in the inlet 2 of the casing 1 and is directed towards the strainer 5, and numeral 14 designates a pipe connected to the vessel 4 and to a vacuum source (not shown).

In the operation of the straining apparatus, a liquid containing fibres or the like enters through the nozzle 13. It is sprayed on the strainer 5, the larger part of the liquid penetrating the strainer, whereas fibres having a length exceeding a certain value (determined with regard to the strainer) are separated and rinsed by following liquid to the sides toward and over the edges of the strainer. The separated fibres and a part of the liquid leave the casing 1 through the outlet 3. For increasing the capacity of the strainer, a sub-atmospheric pressure is maintained in the vessel 4 by its communication through the pipe 14 with a vacuum source.

As can be seen from FIG. 1, the conduit 7 connected to the outlet 6 of the vessel 4 opens outside the casing 1 at a level above the lower strainer 8. This guarantees that a liquid surface will be formed above the strainer 8 and, thus, that a liquid column covers the inlet side of the strainer. During normal operation of the straining apparatus, the liquid level in the vessel 4, owing to the sub-atmospheric pressure therein, will be kept somewhat above the level of the opening of the conduit 7 outside the casing 1.

Owing to the pressure difference prevailing between the inlet side and outlet side of the strainer 5, fibres of a certain length are forced through the strainer 5 together with the liquid. In order that these particles shall be able to pass through the lower strainer 8, the mesh openings of the latter are larger than those of the first strainer 5, as there is not a corresponding pressure difference between the inlet side and outlet side of this lower strainer.

If the first strainer 5 ruptures, the liquid containing long fibres flows directly down into the vessel 4 onto the liquid surface present therein. As soon as the long fibres reach the lower strainer 8, this is obstructed so that the liquid surface in the vessel 4 will be raised. Also the liquid surface in the tube 11 will rise, and when the liquid surface in the vessel 4 has reached a certain level, the liquid will flow over the upper edge of the tube 11. In this way, there is obtained an indication that the strainer 5 has ruptured.

When the liquid supply through the nozzle 13 has been stopped for changing of the strainer 5, the valve 12 at the lower end of the tube 11 is opened. The liquid present within the vessel 4 and the long fibres therein will then flow out through the outlet 9 and further through the conduit 10 and the valve 12. When the liquid surface in the vessel has been lowered sufficiently, liquid will flow through the conduit 7 towards the outlet 6 of the vessel 4. This flow of liquid occurs because of the fact that the end of the conduit 7 situated outside the casing 1 opens at a level situated above the level of the outlet 9 of the vessel 4. Owing to this flow of liquid back through the conduit 7, there is achieved automatically a reverse rinsing of the strainer 8, which is thereby freed from the long fibres by which it had been obstructed. These fibres leave the vessel 4 together with the liquid through the outlet 9.

When the strainer 8 has been freed from fibres in this way, and the first strainer 5 has been changed, the operation of the straining apparatus can be resumed immediately. The liquid surface in the vessel 4 will not be lowered below the lower strainer 8.

We claim

1. In a straining apparatus for separating fibres and the like from a liquid, the combination of a vessel having an outlet, a first strainer forming one wall of the vessel, means for spraying the fibre-containing liquid on to the outside of said strainer wall, means for evacuating said vessel, a second strainer having a smaller total area than the first strainer and covering said outlet from the vessel, said outlet being situated lower than said strainer wall, said second strainer having an inlet side, and means for maintaining, during operation of the straining apparatus, a liquid column covering said inlet side of the second strainer and forming a free liquid surface between the two strainers, the mesh openings of the second strainer being larger than the mesh openings of the first strainer but small enough so that fibres passing through the first strainer due to rupture thereof will rapidly obstruct the second strainer, the combination comprising also an outlet conduit connected to said outlet of the vessel, said conduit having outside the vessel a portion located at a higher level than the second strainer.

2. The combination of claim 1, in which the vessel has a further outlet leading from a point located immediately above the second strainer but below the level of said portion of the outlet conduit.

3. The combination of claim 2, comprising also a second conduit connected at one end to said further outlet, the other end of the second conduit opening freely outside said vessel at a point above the level at which the liquid surface is formed within the second conduit during normal operation of the apparatus.

4. In a straining apparatus for separating fibres and the like from a liquid, the combination of a vessel having an outlet, a first strainer forming one wall of the vessel, means for spraying the fibre-containing liquid on to the outside of said strainer wall, means for evacuating said vessel, a second strainer having a smaller total area than the first strainer and covering said outlet from the vessel, said outlet being situated lower than said strainer wall, said second strainer having an inlet side, and means for maintaining, during operation of the straining apparatus, a liquid column covering said inlet side of the second strainer and forming a free liquid surface between the two strainers, the mesh openings of the second strainer being larger than the mesh openings of the first strainer but small enough so that fibres passing through the first strainer due to rupture thereof will rapidly obstruct the second strainer, the combination comprising also a conduit connected to the vessel immediately above the second strainer and having a lower portion located below the level of the second strainer, and a shut-off valve connected to said lower portion for discharging medium from above the second strainer.

5. In a straining apparatus for separating fibres and the like from a liquid, the combination of a vessel having an outlet, a first strainer forming one wall of the vessel, means for spraying the fibre-containing liquid on to the outside of said strainer wall, means for evacuating said vessel, a second strainer having a smaller total area than the first strainer and covering said outlet from the vessel, said outlet being situated lower than said strainer wall, said second strainer having an inlet side, and means for maintaining, during operation of the straining apparatus, a liquid column covering said inlet side of the second strainer and forming a free liquid surface between the two strainers, the mesh openings of the second strainer being larger than the mesh openings of the first strainer but small enough so that fibres passing through the first strainer due to rupture thereof will rapidly obstruct the second strainer, the vessel having a further outlet above said outlet covered by the second strainer.

* * * * *